US008917395B2

(12) United States Patent
Dalgleish et al.

(10) Patent No.: US 8,917,395 B2
(45) Date of Patent: Dec. 23, 2014

(54) MEMS MICRODISPLAY OPTICAL IMAGING AND SENSOR SYSTEMS FOR UNDERWATER SCATTERING ENVIRONMENTS

(75) Inventors: Fraser Dalgleish, Vero Beach, FL (US); Anni Dalgleish, Vero Beach, FL (US); Bing Ouyang, Vero Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 918 days.

(21) Appl. No.: 13/089,715

(22) Filed: Apr. 19, 2011

(65) Prior Publication Data
US 2012/0069342 A1 Mar. 22, 2012

Related U.S. Application Data

(60) Provisional application No. 61/325,449, filed on Apr. 19, 2010.

(51) Int. Cl.
G01N 21/55 (2014.01)
G01N 21/47 (2006.01)
G01N 21/17 (2006.01)

(52) U.S. Cl.
CPC ........ *G01N 21/47* (2013.01); *G01N 2021/1793* (2013.01); *G01N 2201/0675* (2013.01)
USPC ....................................................... 356/445

(58) Field of Classification Search
CPC ........... G02B 26/0833; G02B 27/0172; G02B 19/0057; G02B 2027/0154; G02B 2027/0178; G02B 26/06; G02B 27/00; G02B 27/0176; G02B 27/0179; G02B 27/108; G02B 27/14; G02B 27/142; G02B 27/145; G02B 27/42
See application file for complete search history.

(56) References Cited

U.S. PATENT DOCUMENTS

| | | | |
|---|---|---|---|
| 3,775,735 A | 11/1973 | Funk et al. | |
| 4,088,898 A | 5/1978 | Stictch | |
| 4,707,128 A | 11/1987 | Coles | |
| 5,046,259 A | 9/1991 | Tusting | |
| 5,418,608 A | 5/1995 | Caimi et al. | |
| 6,072,903 A | 6/2000 | Maki et al. | |
| 6,723,975 B2 | 4/2004 | Saccomanno | |
| 7,355,648 B1 * | 4/2008 | Braun et al. | 348/370 |
| 7,609,875 B2 | 10/2009 | Liu et al. | |
| 2006/0066944 A1 | 3/2006 | Okugawa | |
| 2008/0218821 A1 | 9/2008 | Dalgleish et al. | |

OTHER PUBLICATIONS

Jaffe, J. et al., Underwater Optical Imaging: Status and Prospects, Oceanography, vol. 14, No. 3, 2001 pp. 66-76.
Dalgleish, F. R. and Caimi. F. M., 2011, "Synchronous Laser Line Scanners for Undersea Imaging Applications," Book chapter in Handbook of Optical and Laser Scanning (Stutz, G. E. and Marshall, G. F. (Ed.)) CRC Press, Taylor and Francis Group, Boca Raton, FL.

(Continued)

*Primary Examiner* — Michael P Stafira (57) ABSTRACT

An imaging or sensor system comprises a transmitter assembly, a receiver assembly and a control unit. The transmitter assembly defines an outgoing optical beam transmission path with respect to a target surface and the receiver assembly defines a return optical signal transmission path from the target surface. Each of the paths includes transmission through or reflection from at least one microdisplay device comprising a plurality of controllable elements for selective placement in a transmit mode for transmission of light along the transmission paths. A control unit selectively places the microdisplay device elements in the transmission mode.

19 Claims, 7 Drawing Sheets

(56) References Cited

OTHER PUBLICATIONS

Jaffe, J., Performance bounds on synchronous laser line scan systems, Optical Society of America, Optics Express, vol. 13, No. 3, Feb. 7, 2005, pp. 738-748.

Kulp, T. et al., Development and testing of a synchronous-scanning underwater imaging system capable of rapid two-dimensional frame imaging, Applied Optics, vol. 32, No. 19, 1993, pp. 3520-3532.

Mullen, L. et al., Modulated laser line scanner for enhanced underwater imaging, Proceedings of SPIE, vol. 3761, Airborne and In-Water Underwater Imaging, editor Gary D. Gilbert, Oct. 1999, pp. 2-9.

Duarte, "Single-Pixel Imaging Via Compressive Sampling: Building Simpler, Smaller, and Less Expensive Digital Cameras", IEEE Signal Processing Magazine, Mar. 2008; p. 83-91.

Candes, "Compressive Sampling", IEEE 2006, Proceedings of the International Congress of Mathematicians, Madrid Spain, 2006 European Mathematical Society p. 1-20.

Candes, Robust Signal Recovery From Incomplete Observations, Applied and Computational Mathematics, Caltech Pasadena, CA, IEEE 2006, pp. 1281-1284.

Candes, "Near Optimal Signal Recovery From Random Projections: Universal Encoding Strategies" IEEE 2006 Transactions on Information Theory vol. 52 No.

Donoho, "Compressed Sensing", IEEE Transactions on Information Theory vol. 52, No. 4 Apr. 2006.

Baraniuk, "Compressive sensing", IEEE Signal Processing Magazine (2007) 24: 118-121.

Baron et al., "Distributed compressed sensing", Rice University, Department Electrical and Computer Engineering Technical Report (2006) TREE-0612.

Candes, "Compressive sampling", Proc Int Cong Mathematicians (2006) 3: 1433-1452.

Candes et al., "Sparsity and incoherence in compressive sampling", Inverse Problems (2007) 23: 969-985.

Candes et al., "Stable signal recovery from incomplete and inaccurate measurements", Comm Pure Appl Math (2006) 59(8): 1207-1223.

Carron, "Nuit Blanche", Blog. Retrieved on Oct. 10, 2013, from http://nuit-blanche.blogspot.com/2008/06/cs-another-single-pixel-camera-at-rice.html (3 pages).

Chen et al., "Atomic decomposition by basis pursuit", SIAM J Science Comp.(1999) 20: 33-61.

Dalgliesh et al., "Improved LLS imaging performance in scattering-dominant waters", SPIE (2009) 7317: 73170E.

De Haan et al., "Deinterlacing—An Overview", Proc of the IEEE (1998) 86(9): 1839-1857.

Do et al., "Distributed compressed video sensing", Proc IEEE Int Conf on Image Processing (2009): 1393-1396.

Doyle et al., "Progressive scan conversion using edge information", Signal Processing of HDTV II (1990) 711-721.

Dudley et al., "Emerging digital micromirror device (DMD) applications", Proc of SPIE (2003) 4985: 14-25.

Farouk, "MPEG bit rate improvement using adaptive GOP", International Journal of Circuits, Systems and Signal Processing (2007) 1: 8-11.

Gan et al., "Fast compressive imaging using scrambled block Hadamard ensemble", Proc EUSIPCO (2008) (5 pages).

Kang et al., "Distributed compressive video sensing", Proc IEEE Int Conf on Acoustics, Speech and Signal Processing (2009): 1169-1172.

Lukin, "High-quality spatial interpolation of interlaced video", Proc of Graphicon (2008): 114-117.

Ouyang et al., "Underwater laser serial imaging using compressive sensing and digital mirror device", SPIE(2011) 8037: 803707.

Raginsky et al., "Performance bounds for expander-based compressed sensing in the presence of Poisson noise", Proc Asilomar Conference on Signals, Systems, & Computers (2009) (15 pages).

Tropp et al., "Random filters for compressive sampling and reconstruction", Proc ICASSP (2006): 872-875.

\* cited by examiner

8A Top Level
8B One Block
8C Overall Matrix
8D At Five Attenuation Lengths

FIG. 9A Binary

FIG. 9B Model Predicted

FIG. 12

MEMS MICRODISPLAY OPTICAL IMAGING AND SENSOR SYSTEMS FOR UNDERWATER SCATTERING ENVIRONMENTS

RELATED APPLICATION

This application claims priority to U.S. Provisional Patent Application Ser. No. 61/325,449, filed 19 Apr. 2010 which is incorporated herein by reference in the entirety.

STATEMENT REGARDING FEDERALLY SPONSORED DEVELOPMENT

Development of this invention was supported in part by Award No. N00014-09-1-0714, awarded by the United States Office of Naval Research. Accordingly, the United States Government may have certain rights in this invention.

FIELD OF THE INVENTION

This application relates generally to imaging systems and methods and, in particular, has application in characterization of surfaces, e.g., reflectance profiles, from remote positions wherein visibility through a medium may be range limited or otherwise obscured by, for example, light scattering effects or other phenomena which can limit transmission of optical data. This application also relates to measurement of light scattering characteristics in a medium.

BACKGROUND OF THE INVENTION

In both terrestrial and submarine environments there are situations in which the transmission of imaging information through the field of view is limited rendering it difficult to characterize surfaces with conventional imaging system components such as, for example, a CCD-based imaging device and a divergent illumination source. One common limiting factor is the presence of a large number of suspended particles in the field of view. Not only does this result in significant back scattering of light, but it also contributes to transmission loss of imaging data. Typically, when the predominant component of energy received by the imaging device is attributable to scattered light, the signal-to-noise ratio is too low to provide useful information.

Several designs and configurations have emerged for underwater imaging applications at varied ranges. Conventional camera systems having an adjacent broad spectrum light source are useful for imaging surfaces at distances of one to two attenuation lengths. An attenuation length is the distance light must travel to be reduced to 1/e of its original intensity. The attenuation length is typically 20 to 30 m in clear water. It has been found that at distances of about three attenuation lengths, acceptable imaging can be provided by spatially separating the light source from the camera, e.g., using a flood light to illuminate the target region.

At imaging distances greater than three attenuation lengths, laser-based systems are more effective. These extended range imagers are generally of two classes: the synchronous laser line scanner (LLS) and the range gated scanner. See Jaffe, J. S. et al. "Underwater Optical Imaging: Status and Prospects", Oceanography, Vol. 14, No. 3 pp. 66-76 (2001). See, also, U.S. Pat. Nos. 4,707,128 and 5,418,608 each of which is incorporated herein by reference. These types of imaging systems can provide acceptable real-time image data in the range of 3 to 7 attenuation lengths. Such imagers have been under continued development for use in Autonomous Underwater Vehicles (AUVs) and Remotely Operated Underwater Vehicles (ROVs) to provide surface information needed for navigation as well as for characterizing the sea floor for varied activities including military missions and construction of oil and gas infrastructures.

Synchronous LLS systems provide scanning capability with a continuous wave (CW) laser source. Based on results of controlled experimentation and analytical modeling, synchronous scanners have been found capable of operation at maximum distances of about 5 to 6 attenuation lengths. Further improvement in imaging range would benefit undersea operations by allowing increased vehicle speed and maneuverability and improved image resolution at greater distances from target regions. By way of example, in the exploration of unknown or dynamic environments, rapid topographical seabed variations can occur at rates greater than the vertical axis performance of the AUV. It is therefore necessary to distance the vehicle at a sufficient range above the seabed to avoid potentially catastrophic collisions. Optimal underwater optical scanner designs must consider this AUV trajectory.

The ability to more rapidly produce higher resolution images of targets and survey sites from greater distances will enable a more extensive and diverse set of applications for underwater vehicles. Depending on the size and complexity of surfaces in the target region, optical sensing may be the only effective means for characterizing features.

It has also been shown by both simulation and experimentation that the class of range-gated imagers i.e., those imagers utilizing a pulsed laser source, may be capable of adequate underwater performance for imaging target regions at distances up to seven attenuation lengths. These systems minimize introduction of energy due to scattered light with gating electronics. Although these imagers ultimately become power (or photon)-limited due to the exponential decay rate of light traveling through the water, they can be more compact than CW LLS systems because a spatial offset between the source and receiver is not required to reject scattered light.

Summarily, both classes of extended range underwater imagers ultimately are limited in range by the cumulative effects of forward scattering events and divergence of the illumination, particularly as the reflected signal travels from the target region to the imaging system. Scattering causes losses in contrast, resolution and signal to noise ratio (SNR). These losses are particularly problematic at and near the range limit of operation.

Relatively small depth of field (DOF) has also been a disadvantage in prior LLS system designs. This is particularly problematic when imaging in a dynamic undersea environment in which there is significant variation in ef optical transmission properties or in sea bed surface features or in which there is significant variation in platform altitude or attitude. With a small DOF each of these factors can lead to unacceptable degradation in image quality or complete signal loss. The DOF is a function of the source-receiver separation distance, the optical path length to and from the target, beam divergence and the acceptance angle of the receiver. The receiving aperture of the LLS system may be widened to improve DOF. Alternately, a fine adjustment of the optical focus may be slaved in accord with an on-board altimeter.

Range-gated imagers have also had inherent disadvantages in addition to limitations in imaging distance. For example, variations in distance between the system and a target surface result in a change in the required delay time of the gating function used to selectively acquire photons returning from the target.

Based on the foregoing it is apparent that both classes of extended range imagers have performance limitations restricting usefulness in a variety of potential applications including, for example, smoke-filled environments, fog, adverse weather conditions and underwater imaging. In addition, the size, weight and power requirements are also extremely important when designing an imager for portable or mobile deployment in any of the afore-described environments.

The optical resolution achievable with a LLS system is dependent on the laser beam diameter at the reflecting surface in the target region, and is also dependent upon the precision with which the receiver can resolve intensity information from the return signal as a function of the scan angle. Minimizing the instantaneous field of view (IFOV), e.g., by minimizing the spot size at the target, reduces the scattering volume, which reduction can improve the signal-to-noise ratio. That is, the imaging range of the system can be improved by reducing the size of the scattering volume. Reducing the IFOV reduces the target area per pixel, commonly measured in $cm^2$ per pixel and, theoretically, improves image resolution. This is particularly desirable when imaging target surfaces having a high spatial frequency, as the combined effects of forward scattering and blurring, due to the limited DOF, further limit the achievable resolution.

The '821 Patent describes a synchronized laser beam scanning system in which the scanning architecture is built around a single six faceted polygonal scan mirror. The system provides a very narrow instantaneous field of view (IFOV) at the receiver channel which is optically coincident with the outgoing laser pulse throughout the entire scan angle for a fixed stand-off distance. Using two symmetrical steering mirror assemblies, one for the outgoing beam and one for the returning signal, optical synchronization can be maintained as the stand-off distance is adjusted. The symmetry of the source and receiver channels about the center axis of the polygon also significantly reduces the necessary size of the detector photocathode area required to complete a full scan through a wide angle. Polygonal mirror systems are widely used in other laser scanning systems. See, for example, U.S. Pat. No. 6,723,975. However, provision of mechanically rotatable polygonal mirrors in scanners poses a significant addition to the system cost and may affect reliability. Efforts to build small, more compact laser line scanners of this type are subject to limitations because of the mechanical nature of the rotating mirror systems.

U.S. Pat. No. 7,609,875, referred to herein as the '875 Patent, also incorporated herein by reference, discloses a Micro-Electro-Mechanical Systems (MEMS) based laser scanning system having a MEMS mirror which can oscillate in two independent directions. A high speed modulated or pulsed laser beam is transmitted through a fiber collimator and is then radiated toward the MEMS mirror which reflects the beam through a fixed optical path, consisting of a beam splitter, a lens and a static mirror, to the target. Light reflected from the target traverses the same fixed optical path in a reverse direction before entering the receiver. The system as disclosed in the '875 Patent does not include any measures to mitigate signal impairment due to volume backscattering or other light scattering phenomena.

SUMMARY OF THE INVENTION

In accord with one example embodiment there is provided an imaging system having a transmitter assembly, for defining an outgoing optical beam transmission path with respect to a target surface, and a receiver assembly for defining a return optical signal transmission path from the target surface. Each of the two optical transmission paths includes transmission through or reflection from at least one microdisplay device comprising a plurality of controllable elements for selective placement in a mode for transmission of light along the transmission paths. A control unit for selectively placing microdisplay device elements in the transmission mode.

According to another embodiment a method is provided for measurement of the scattering characteristics of a medium. Collimated light is transmitted through a scattering medium so that the light experiences spatial or temporal dispersion while traveling through the medium. The light is received on a light sensitive detector. After the light travels through the medium both direct and scattered components of the light are focused on a plane which provides a Fourier transform plane on which angular information incident on the lens 224 is transformed to spatial frequency. The microdisplay device is positioned along the plane to selectively reflect light incident thereon and control the direction of reflection of the incident light. A portion of the reflected light is directed to a light sensitive detector for measurement while not directing other portions of the reflected light for receipt by the detector.

BRIEF DESCRIPTION OF THE DRAWINGS

Features of the invention will be best understood when the following detailed description is read in conjunction with the accompanying drawings wherein.

Like reference numbers are used throughout the figures to denote like components. Numerous components are illustrated schematically, it being understood that various details, connections and components of an apparent nature are not shown in order to emphasize features of the invention. Various features shown in the figures are not shown to scale in order to emphasize features of the invention.

DETAILED DESCRIPTION OF THE INVENTION

Before describing in detail the particular methods and apparatuses related to embodiments of the invention, it is noted that the present invention resides primarily in a novel and non-obvious combination of components and process steps. So as not to obscure the disclosure with details that will be readily apparent to those skilled in the art, certain conventional components and steps have been omitted or presented with lesser detail, while the drawings and the specification describe in greater detail other elements and steps pertinent to understanding the invention. Further, the following embodiments do not define limits as to structure or method according to the invention, but only provide examples which include features that are permissive rather than mandatory and illustrative rather than exhaustive.

The embodiments described herein are based in part on concepts disclosed in US Patent Application Publication No. 20080218821, now incorporated herein by reference, titled "Method and Apparatus for Synchronous Laser Beam Scanning" and referred to herein as the '821 Patent.

While not limited to such, the concepts and designs now described apply to imaging and sensor systems and are particularly useful in environments characterized by light scattering. Embodiments of the invention have application in systems such as flash LIDAR (Light Detector and Ranging) systems and LLS (laser line scanner) systems where sensing of light reflected from the target can be impaired by scattering and wherein use of adaptive sampling schemes are advantageous. Other sensing applications include systems and methods for measurement of angular and spatial dependence of scatter, such as determination of the volume scattering function (VSF), requiring high dynamic range, high angular resolution and adaptive control capabilities.

Imaging and sensor systems according to the invention are based, in part, on principles outlined in the '821 Patent to maintain optical synchronization between transmitted and received signals and to minimize the receiver IFOV so that interference from volume backscattering can be minimized. According to one series of embodiments, a pair of microdisplay devices are used in lieu of a mechanically rotating polygonal mirror to achieve synchronization. As used herein, the term "microdisplay devices" refers to members of the family of microchips which can be electronically controlled to spatially modulate reflection of light signals, e.g., as commonly used to project an image on a screen or to illuminate a target region. Most microdisplay devices are fabricated with standard CMOS technology, rendering volume manufacture both reliable and economical. Among the variety of microdisplay devices, there are MEMS scanning mirrors, Digital Micromirror Devices (DMD's), Liquid Crystal on Silicon (LCOS) devices and High Temperature Poly-Silicon (HTPS) panel (also known as LCD panel) devices. Since a variety of the microdisplay devices operate according to different mechanisms, different optical configurations may be required to incorporate these into imaging and scanning systems according to the invention, and a variety of system designs may be constructed according to the teachings provided herein.

It is suggested in the '821 Patent that the receiver should provide a resolution of $\frac{1}{1000}$ radian. With arrays having elements on the order of 1920×1080, all of the aforementioned microdisplay devices are capable of providing at least this resolution. Therefore all these types of devices or a combination of them can be used to synchronize transmitter and receiver signals. In accord with embodiments of the invention, additional DMD, LCOS or HTPS devices may be cascaded and used additively to spatially modulate (e.g., transmit or block) light transmission along an optical path to thereby further minimize the receiver IFOV to any given precision.

One of the embodiments based on DMD's is a system which includes a first DMD positioned in a light transmission path and a second DMD positioned in a return signal (receiver) path. Such an example embodiment is now described with the understanding that this is exemplary of one implementation of the inventive concepts. Each DMD comprises a plurality of micro mirrors that can be individually controlled, e.g., turned on or turned off, to direct light toward or away from a receiving lens, to either allow illumination of a spatial location or allow receipt of light signals reflected from the spatial location. In principle a similar approach may be effected with LCOS and HTPS devices. A MEMS scanning mirror can also be used to control transmission or receipt of signals from discrete spatial locations, and this may be effected in a sequential manner.

Figure 1:
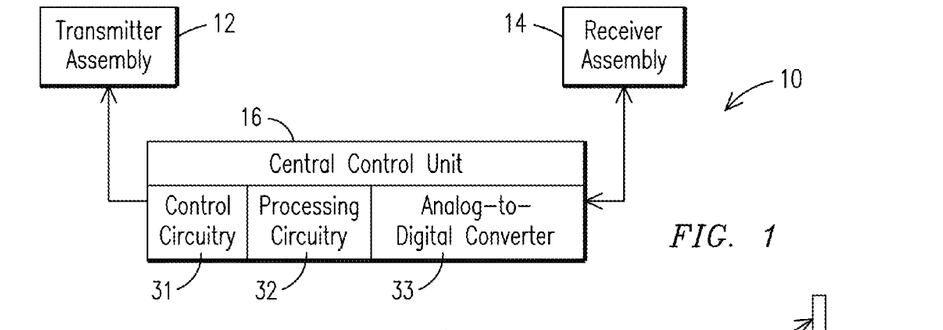
FIG. 1 is a simplified block diagram illustrating an imaging system according to an embodiment of the invention.
Figures 2, 3:
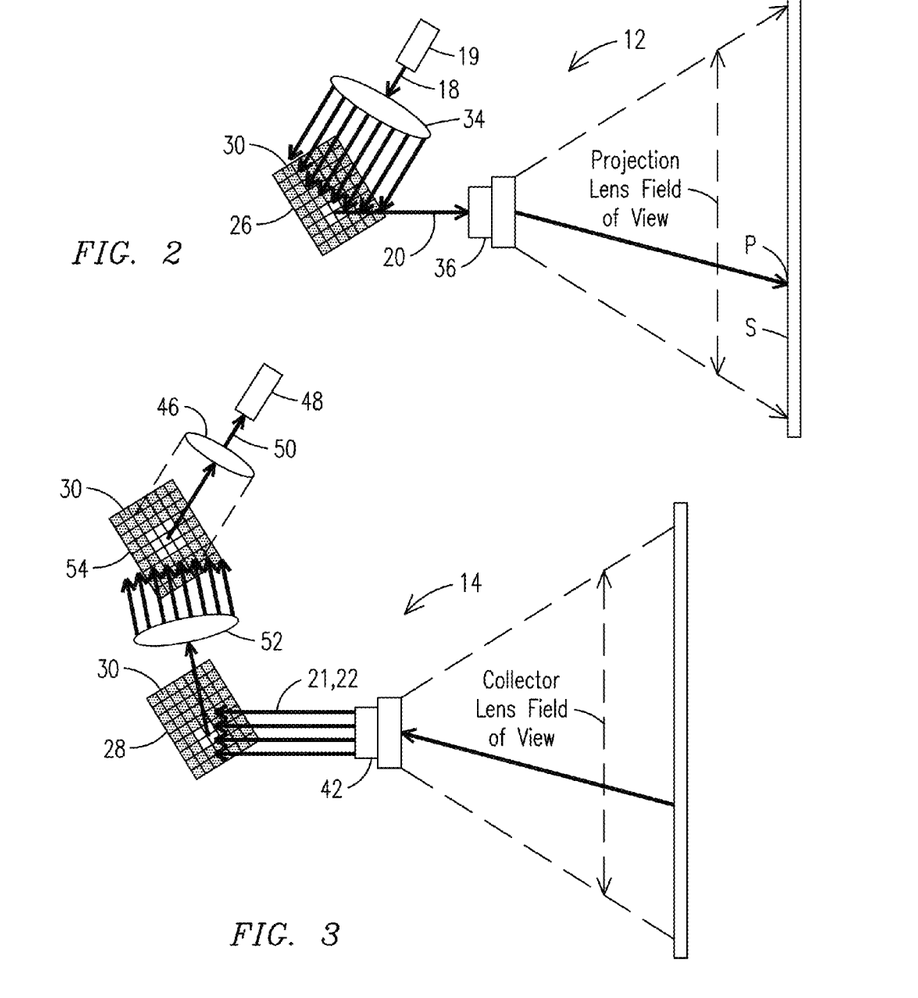
FIG. 2 is a schematic view of the transmitter assembly of the system shown in FIG. 1.
FIG. 3 is a schematic view of the receiver assembly of the system shown in FIG. 1.
Figure 4:
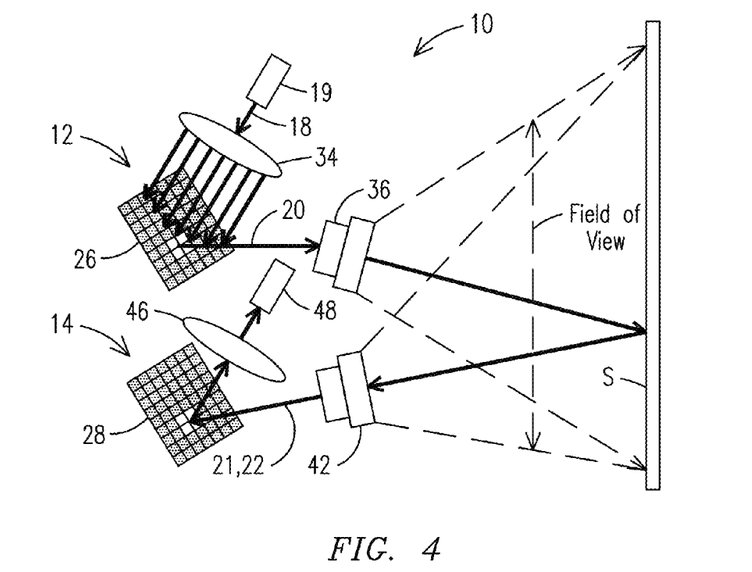
FIG. 4 is a schematic view of showing both the transmitter assembly and receiver assembly and associated optical transmission paths.

With reference to FIGS. 1-4, an imaging system 10 comprises a transmitter assembly 12 and a receiver assembly 14 operable under the control of a central control unit 16 as shown in the block diagram of FIG. 1. With reference to FIG. 2, the transmitter assembly 12 receives a light beam 18 generated by a laser source 19 which propagates along an outgoing optical beam transmission path 20 indicated by arrows in FIG. 2 to a target surface, S. The receiver assembly 14, shown in FIG. 3, receives a light signal 21 reflected from the target surface S which propagates along a return (receiving) optical signal transmission path 22 indicated in FIG. 3 by arrows. The transmitter assembly 12 includes a transmitter DMD 26 positioned in the outgoing beam transmission path 20. The receiver assembly 14 includes a receiver DMD 28 positioned in the return signal transmission path 22.

In this example and in other disclosed embodiments, each DMD is of a conventional design, comprising an array of mirror elements 30 arranged in rows and columns. Each mirror element can be individually selected to move from a blocking position to a transmit position. When in the blocking position a mirror element reflects none, or substantially none, of the received light along a defined transmission path. For example, when a mirror element 30 of the DMD 26 is not selected, it remains in the blocking position so that it reflects none, or substantially none, of the light beam along the outgoing optical beam transmission path 20. Similarly, when a mirror element 30 of the DMD 28 is not selected, it remains in the blocking position so that it reflects none, or substantially none, of the light signal 21, received by the receiver assembly 14 from the target surface, along the return signal transmission path 22.

In an initial state one or both of the DMDs 26, 28 may be in a non-transmitting off state wherein all of the mirror elements in the DMD array are in the blocking position, thereby preventing transmission through the optical paths 20, 22. As used herein the term transmit angle refers to predetermined angle at which each mirror element 24 in a DMD can be selectively placed in order to effect reflection of light in and along an optical transmission path. When a DMD is in the off state none of the mirror elements are selected to be placed at the transmit angle. When one or more mirror elements are selected to be positioned at the transmit angle, they are referred to as being in a transmit mode, while the other mirror elements are referred to as being in a blocking mode because they are not configured to reflect light along the optical transmission path. As used herein, the term pointing angle refers to the angle of the outgoing light beam relative to the center of the projection axis. In the figures individual mirror elements 30 which are in the blocking mode are illustrated with shading while individual elements 30 which are in the transmit mode are illustrated without shading.

The central control unit 16 comprises control circuitry 31, processing circuitry 32 and an analog-to-digital converter 33. The processing circuitry 32 effects data collection and post processing for image generation and enhancement. The control analog-to-digital converter 33 receives an analog output from a photomultiplier detector in the receiver assembly 14.

The control circuitry 31 of the central control unit 16 controls movement of the mirror elements of the DMD's in the system 10. Specifically, the control unit defines a pointing angle of the light beam 18 with respect to the target surface S by placing one or more of the elements 30 of the DMD 26 in a transmit mode so that, at any given time, only selected mirror elements in the DMD 26 are placed in the transmit mode, i.e., to reflect a portion of the light beam along the optical path 20. With this capability the size and the pointing direction of the light beam are controllable. By way of example, a row-by-row and element-by-element selection of adjacent elements 30 can create a raster-like scan pattern along the target surface S. In one embodiment, such a scan sequentially and individually places each element 30 in the transmit mode while all other mirror elements are in the blocking mode. Alternately, the control unit may define groups of adjoining elements 30 and sequentially place groups adjoining or overlapping groups elements 30 in the transmit mode. When each group of elements 30 is selected to be in the transmit mode all other mirror elements are in the blocking mode.

A scan which sequentially and individually places individual elements 30 in the transmit mode is a serial selection of individual elements which sequentially progresses from a first element in a first row to an adjacent element in the same row, then sequentially performing the same serial progression in each other row where row selection progresses serially from the first row to an adjacent row so that the progression moves element by element from the first row to the last row.

When the control unit defines a sequence of segments, each comprising multiple adjoining mirror elements 30, e.g., based on overlapping groups of adjoining elements 30, the beam throughput can be increased. For example, a first segment may comprise four elements 30, where two of the elements are in one row and two of the elements are in an adjacent row such that each element is adjacent two other elements. A second segment in the sequence may comprise two of the same elements of the first segment, but which are in different rows, and two new elements which each are in different rows from one another but next to one of the two elements which were also in the first segment. Generally, as used herein, the term segment refers to one element 30 or a group of adjacent elements 30 which are simultaneously placed in the transmit mode to effect propagation of a light beam or a light signal along a transmission path. For the DMD 26 each segment may be one in a sequence of segments that create a beam scan with, for example, the light beam 18.

Prior to placing each segment of mirrors of the DMD 26 in the transmit mode, the control unit 16 computes the corresponding IFOV of the receiver assembly 14 for that particular segment of mirrors based on (i) the selected size of the light beam transmitted to the target surface S (i.e., determined by the number of adjoining mirror elements placed in the transmit mode), and (ii) the pointing angle of the light beam reflected by the DMD 26 (i.e., an angle which varies based on the location of the selected element(s) in a segment).

Also, with respect to each segment in the sequence of segments defined in the DMD 26, (i.e., the segments to be placed in the transmit mode), the control unit 16 identifies and selects a set of mirror elements 30 of the DMD 28 which elements form a segment in the receiver DMD 28 corresponding to the selected segment. The mirror elements in each identified segment are selected such that the effective field of view of the receiver assembly 14 is adjusted with the DMD 28 to correspond to the computed IFOV. In the illustration of FIGS. 2 and 3 the segments of elements shown as selected to be in the transmit mode for both the transmit assembly 12 and the receiver assembly 14 are shown to be different, i.e., shown to cover different areas of the DMDs, but this is only an example embodiment and different or the same segments may be defined for each DMD.

As the control unit 16 places each segment of the DMD 26 in the transmit mode it also places the corresponding segment of the DMD 28 in the transmit mode to provide a complete optical path wherein the receiver assembly 14 has a time varying, e.g., programmable, field of view based on the computed IFOV.

The control unit 16 may also re-define the size of the selected segment of the DMD 28, i.e., to include more or fewer mirror elements 30, to expand or further limit the IFOV of the receiver. The control unit also performs numerous tasks common to image processing, including operation of the A/D Converter which receives signal information from the receiver assembly (e.g., via a photomultiplier tube) to record the return signal strength. Real-time and automated image adjustment becomes available because the field of view of the receiver assembly 14 is programmable in accord with selection of mirror elements of a DMD device. In addition, the control unit 16 can perform post processing such as filtering to reduce image noise and enhance image contrast to further enhance the signal to noise ratio (SNR). In the illustrated examples the control unit also provides display and image control via drivers and image enhancing software.

The transmitter assembly 12 further comprises a laser beam expander 34 and a projection lens 36 for imaging along the target surface. The transmission path 20 extends from the laser source 19 through the beam expander 34 to the DMD 26 such that the expander illuminates the surface of the DMD which faces the expander with the light beam 18. All of the reflective surfaces of the mirror elements 30 receive a portion of the light beam 18. As discussed above, with a sequence of segments of mirror elements placed in the transmit mode by the control unit 16, portions of the beam 18 are sequentially reflected from the surface by segments of mirror elements 30 which receive the beam so that the transmission path 20 extends from the reflective surface of the DMD 26, through the projection lens 36 and to the target surface S. Accordingly the surface S is illuminated by the light beam 18.

The central control unit turns on a selected segment of the mirror elements 30 (e.g., a single mirror element, a row of mirror elements or some predetermined or randomly generated pattern of elements) of the DMD 26 so that mirror elements in the selected segment transition from the blocking mode to a preset transmit angle for the transmit mode, thereby illuminating a portion of a target surface S. As shown in FIG. 2, the projection lens 36 transmits a portion of the light beam 18 from a selected segment, e.g., segment 30T, at a predetermined pointing angle to illuminate a portion P of the target surface S. In this context the pointing angle refers to the angle of the outgoing light beam relative to the optical axis of the projection lens 36.

By way of example, it is to be understood that if each segment of mirror elements is a horizontal row of mirror elements in the transmitter DMD 26 then, by sequentially selecting adjacent elements in adjacent horizontal rows of the DMD 26, the mirror elements 30 are used to serially transmit full lines of laser light, and the transmitter assembly performs a line scan sweep along the target surface S commensurate with the projection lens field of view.

With reference to FIG. 3, embodiments of the receiver assembly 14 include a lens 42 functioning as a 'bucket' collector for collecting and focusing photons emanating from the target surface S on to the mirror elements 30 of the receiver DMD 28. The lens 42 may be a single plano-convex lens. The receiver assembly also includes a focusing lens 46 and a photomultiplier tube 48 having a photocathode. The focusing lens 46 condenses the light signal 21 on to the photocathode. The receiver assembly may optionally include, as shown in FIG. 3, an additional magnifying lens 52 and a reshaping DMD 54.

As the transmitter assembly 12 performs a scan along the target surface S, the receiver assembly 14 collects and focuses photons emanating from the target surface on to the mirror elements 30 of the DMD 28. A feature of the example embodiments is that unwanted light, (i.e., light which has either been scattered with the medium or scattered during propagation along the transmission path and reflected from an adjacent target region) can be eliminated at the receiver DMD 28. Elimination is effected by programming the receiver DMD 28 with the control unit 16 to effectively reduce the field of view of the receiver assembly 14. As described above, each time a segment of elements 30 of the transmit DMD 26 is placed in the transmit mode, only a segment of the DMD 28 which corresponds to the IFOV of the selected segment of the DMD 26 is placed in the transmit mode. In this way, as the control unit 16 sequentially places segments of mirror elements of the DMD 26 in the transmit mode, the receiver assembly 14 operates as a moving iris, letting through desirable (e.g., non-scattered) photons from the target surface while blocking most or all of the scattered light from reaching the photocathode of the photomultiplier tube 48. Programmability of the DMD 28 also enables the system 10 to adapt to scan deviations. These features alleviate the need for sophisticated optical synchronization, as has been required in the case of systems operating with steerable mirrors, as well as the need to use a spinning aperture to account for cross-axis scan deviations.

The transmission path 22 extends from the collector lens 42 which receives photons emanating from the surface S illuminated by the laser source 19. The path 22 continues to the receiver DMD 28 such that the surface 56 of the DMD 28 which faces the lens 42 receives the light signal 21. All of the reflective surfaces of the mirror elements 30 of the DMD 28 may receive a portion of the light signal 21. As discussed above, with segments of mirror elements of the DMD 28 sequentially placed in the transmit mode by the control unit 16, portions of the light signal 21 are sequentially reflected from the surface 56 by different segments of mirror elements 30 so that the transmission path 22 extends from the reflective surface 56 of the DMD 28, through the magnifying lens 52 to a reflective surface 60 of a reshaping DMD 54. The reshaping DMD 54 and the magnifying lens 52 are used to reshape the IFOV to any desired geometric region. To effect this functionality the control unit 16 defines mirror segments comprising elements 30 of the DMD 54 which correspond to those spatial regions in the field of view having undesirably high levels of backscattering. According to embodiments of the invention the control unit configures the defined segments in a blocking mode while all other mirror elements 30 are placed in the transmit mode. With this configuration the spatial regions having undesirably high levels of backscattering are removed from the field of view before the light signal propagates to the photomultiplier tube 48. Accordingly, only portions of the light signal 21 containing acceptably low levels of backscattering are reflected by those mirror elements of the DMD 54 which the control unit selects to be in the transmit mode, thereby allowing those portions of the light signal to propagate along the transmission path 22 and through the focusing lens 46 so that the condensed light signal 21 strikes the photocathode 50 of the photomultiplier tube 48. The analog voltage output from the photomultiplier tube 48 is sent into the analog-to-digital converter 33 in the central control unit 16 for data collection and post processing. Another feature of the illustrated embodiment is that all of the light which can be transmitted from all of the mirror segments 30 on the reshaping DMD 54 can be focused on the photocathode 50 of the photomultiplier tube 48. Consequently only one photomultiplier tube 48 is required in the system 10. This feature facilitates further reduction in system size and cost.

Figure 5:
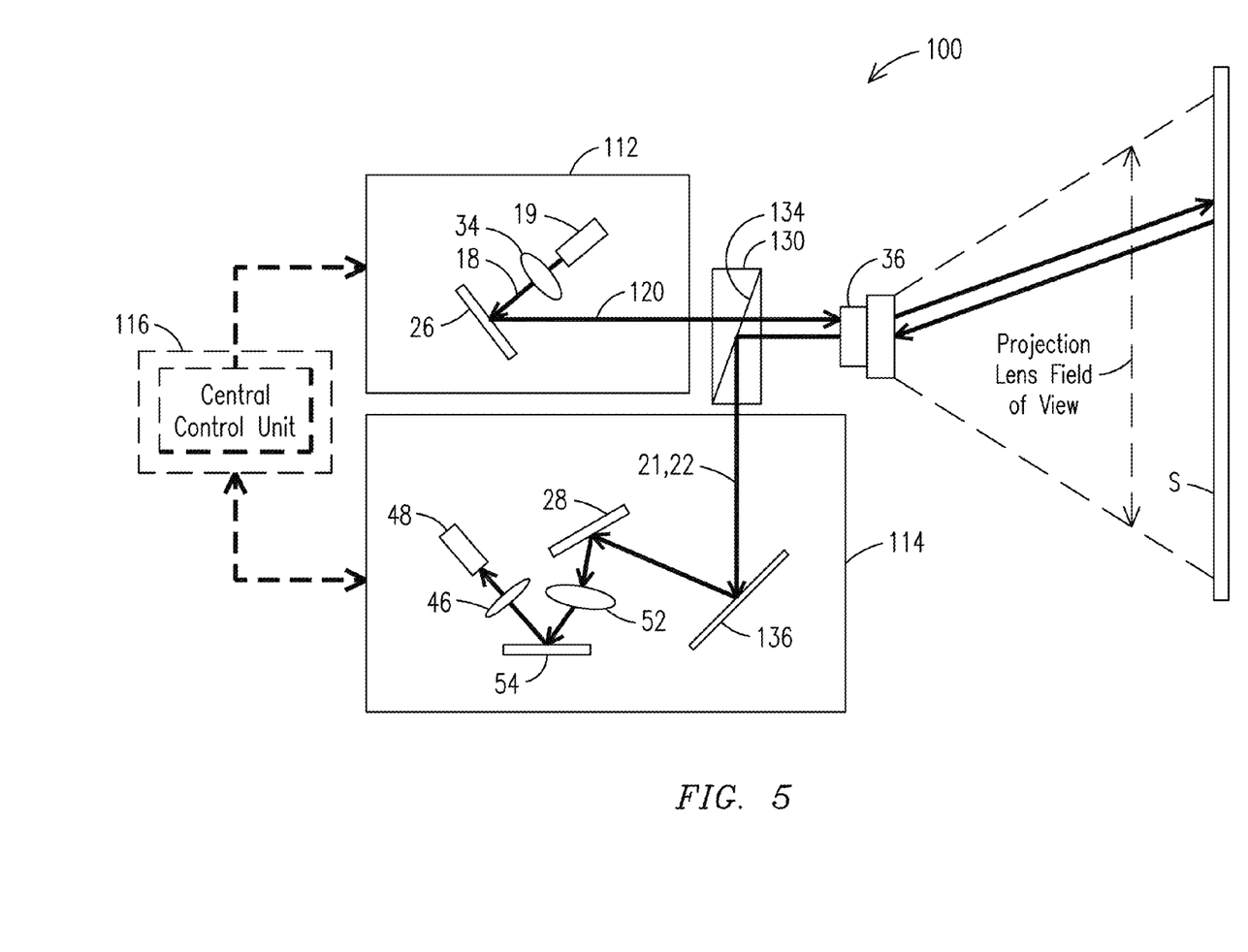
FIG. 5 illustrates an imaging system according to another embodiment of the invention.

FIG. 5 illustrates an imaging system 100 comprising a transmitter assembly 112 and a receiver assembly 114 operable under the control of the central control unit 16 as described with respect to FIGS. 1-4. In this regard, like reference numbers used for the features of the system 10 denote like features in the system 100. The transmitter assembly 112 transmits a light beam 18 generated by a laser source 19 which propagates along an outgoing optical beam transmission path 120 as indicated by arrows to a target surface, S. The receiver assembly 114 receives a light signal 21 reflected from the target surface S which propagates along a return (receiving) optical signal transmission path 122 as indicated by arrows. The transmitter assembly 112 includes the transmitter DMD 26 positioned in the outgoing beam transmission path 120 and the receiver assembly 114 includes the receiver DMD 28 positioned in the return signal transmission path 122. The system 100 does not include a collector lens 42 as a distinct component of the receiver assembly 114. Rather, the projection lens 36 is an element common to both of the transmission paths 120 and 122. Functionally the optical transmission paths 120 and 122 are each the same as a corresponding one of the paths 20 and 22. However, in the path 122 the light signal 21 propagates from the surface S through the projection lens 36 instead of passing through a collector lens 42. This arrangement is effected with positioning of a Total Internal Reflection (TIR) prism 130 placed in a segment of the transmission paths between the lens 36 and the two assemblies 112 and 114 so that the laser light beam 18 passes from the transmitter DMD 26 through the prism 130 to the projection lens while an internal surface 134 of the prism 130 reflects the light signal 21, emanating from the surface S and passing through the projection lens 36. The light signal 21 is reflected by the internal surface 134 to propagate to a mirror 136 which reflects the light signal 21 to the receiver DMD 28. Thus the two optical paths share a common segment extending from the prism 130 to the lens 36 and to the target surface S. By adding the TIR prism 130 in the optical paths, the light beam 18 emitted from the transmitter assembly 112 illuminates the target surface S and the light signal 21 reflected back from the target surface S is directed into the receiver assembly 114.

Microdisplay devices other than DMD's, such as LCOS or HTPS devices, can be used in the systems 10 and 100 or variations thereof. The same optical configurations as shown in the figures can be used without change for several reflective type devices such as LCOS and MEMS scanning mirror devices. When incorporating a transmission type HTPS device, the laser source 19 and the photomultiplier tube 48 may be placed behind the HTPS panels. In the illustration of the systems 10 and 100 only one level of magnification is provided by cascading the one reshaping DMD 54 in the receiver assembly 14 or 114. However, multiple stages of magnification can be achieved by cascading two or more shaping DMD's 54 in the receiver optical path.

Compressive Sensing (CS) is a known framework for the simultaneous sampling and compression of sparse, and therefore compressible, signals using incomplete, non-adaptive linear measurements [3-6]. See D. Donoho, "Compressive Sensing," IEEE Trans. Inform. Theory, vol. 52, pp. 1289-1306, 2006; E. Candes and T. Tao, "Near Optimal Signal recovery From Random Projections: Universal Encoding Strategies," IEEE Trans, Inform. Theory, vol. 52, pp. 5406-5425, 2006; and E. Candes, "Compressive Sensing;", Proc. Int Cong. Mathematicians, vol, 3, pp 1433-1452, 2006.

An N-pixel signal $$X=\{X(n), n=1,2,\ldots N\}$$

is said to be K-sparse if there exists an N-dimensional sparsifying basis $$\Psi=\{\psi_1, \psi_2 \ldots, \psi_N\}$$

and if $$X=\Psi a,$$

where the N×1 vector a contains K<<N non-zero entries.

CS theory states that if such a K-sparse basis exists for X, then X can be recovered with overwhelming probability using more than M=O(KlogN) incoherent linear measurements:

$$Y=\Phi X=\Phi \Psi a,$$

where Y is a M×1 vector and $\Phi$ is a M×N matrix that is incoherent with the sparsifying matrix $\Psi$. See, again, E. Candes, "Compressive Sensing,", Proc. Int Cong. Mathematicians, vol. 3, pp 1433-1452, 2006. The matrix $\Phi$ is referred to as the measurement matrix. See E. Candes and J. Romberg, "Robust Signal Recovery from Incomplete Observations," Proc. ICIP, pp. 1281-1284, 2006.

The incoherent property can be satisfied if the maximum magnitude of the elements of $\Phi \Psi$ is small See L. Gan, T. Do and T. Tran. "Fast compressive imaging using scrambled block Hadamard ensemble". Proc. EUSIPCO, 2008. This condition can be achieved if is random based, such as in a pseudo-random sequence, Bernoulli binary vectors or scrambled block Hadamard Ensemble (see M. Duarte, M. Davenport, D. Takhar, J. Laska, T. Sun, K. Kelly and R. Baraniuk, "Single-Pixel Imaging via Compressive Sensing," IEEE Signal Processing Magazine, vol. 25, pp. 83-91, 2008), whereas K-sparse sparsifying basis $\Psi$ exists for many signal types, for example, natural images are sparse in Fourier, DCT or wavelet domain, a property exploited in the compression standards such as JPEG and JPEG2000. The $l_1$ norm minimization (see E. Candes and J. Romberg, "Sparsity and incoherence in compressive sampling," Inverse Problems, vol. 23, pp. 969-985, 2007) can recover a (therefore X) from the measurements Y:

$$\hat{\alpha} = \arg \min \|a\|_1$$

subject to $Y=\Phi \Psi a$ (1)

where $$\|a\|_1 = \sum_{i=1}^{N} |a_i|$$

is the $l_1$ norm of a. Such an optimization problem is called basis pursuit.

The application of CS theory in image and video applications, or Compressive Imaging (CI) is one area of extensive interest. In addition to the aforementioned sparsifying basis, the image gradient sparsity can also be exploited via minimization of the image total variation (TV). For a digital image X, at pixel location $x_{ij}$, the discrete gradient $D_{ij}(X)$ is defined as:

$$D_{ij}(X) = \begin{pmatrix} D_{h;ij}(X) \\ D_{v;ij}(X) \end{pmatrix} \quad (2)$$

$$D_{h;ij}(X) = x_{i+1,j} - x_{i,j}$$

$$D_{v;ij}(X) = x_{i,j+1} - x_{i,j}$$

Then the TV of X is the sum of the magnitudes of $D_{ij}(X)$ at every point in X:

$$TV(X) = \sum_{ij} \sqrt{D_{h;ij}(X)^2 + D_{v;ij}(X)^2} \quad (3)$$

TV minimization with quadratic constraints has been shown to provide better visual quality than that $l_1$ optimization [12] when recovering images from noisy observations:

$$\min TV(X)$$

subject to $\|\Phi X - Y\|_2 \leq \epsilon$ (4)

Figure 6A:
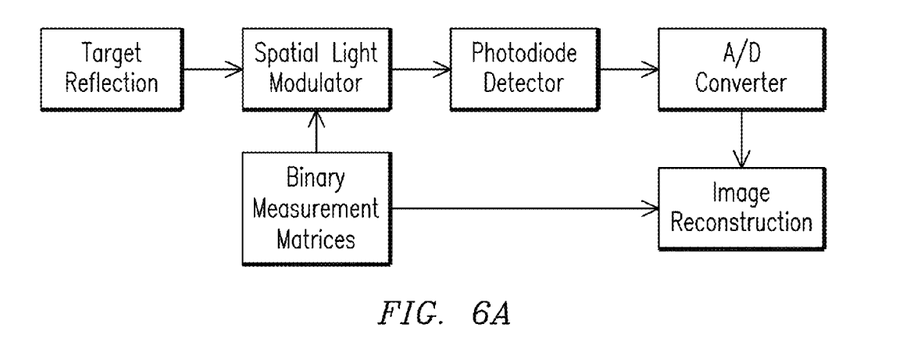
FIG. 6A is a flow diagram which illustrates an architecture for a one pixel compressive sampling camera.

So far CS based imagers have been developed for various research disciplines. Among them, Rice University's one pixel camera and variations are the earliest implementation. See, again, M. Duarte, M. Davenport, D. Takhar, J. Laska, T. Sun, K. Kelly and R. Baraniuk, "Single-Pixel Imaging via Compressive Sensing," IEEE Signal Processing Magazine, vol. 25, pp. 83-91, 2008.

The target reflection is modulated with a series of measurement basis $\Phi$; and the measurement for each of the bases is recorded by a photon counter. M measurements $$Y\{y(l), l=1 \ldots M\}$$

are obtained in serial. $\Phi$ and Y are then used as inputs to an optimization reconstruction process to recover á and the image X. An active illumination based one pixel camera was also reported by them. See, again, M. Duarte, M. Davenport, D. Takhar, J. Laska, T. Sun, K. Kelly and R. Baraniuk, "Single-Pixel Imaging via Compressive Sensing," IEEE Signal Processing Magazine, vol. 25, pp. 83-91, 2008. See, also, the flow diagram of FIG. 6A which illustrates the Rice One Pixel CS Camera Architecture.

Figure 6B:
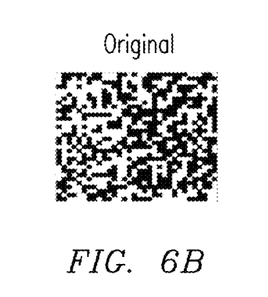
FIGS. 6B and 6C illustrate a binary measurement pattern before and after propagation through water.
Figure 6C:
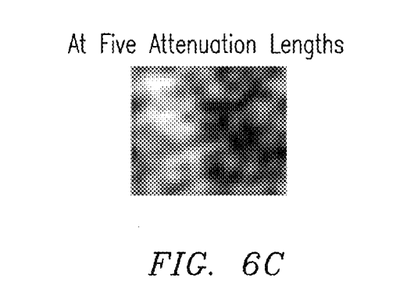

According to the invention, a CS based underwater imaging system is presented for use in an underwater environment, where any imaging system is subject to the dispersive water medium. There is not an exception for a CS based imaging system. The binary measurement matrices generally used in an over-the-air imaging system will lose most of the detail after propagating short distances in the water. FIGS. 6B and 6C illustrate degradation of an image shown in FIG. 6C at five attenuation lengths as shown in FIG. 6C, which renders the spatial light modulation ineffective.

Figure 7A:
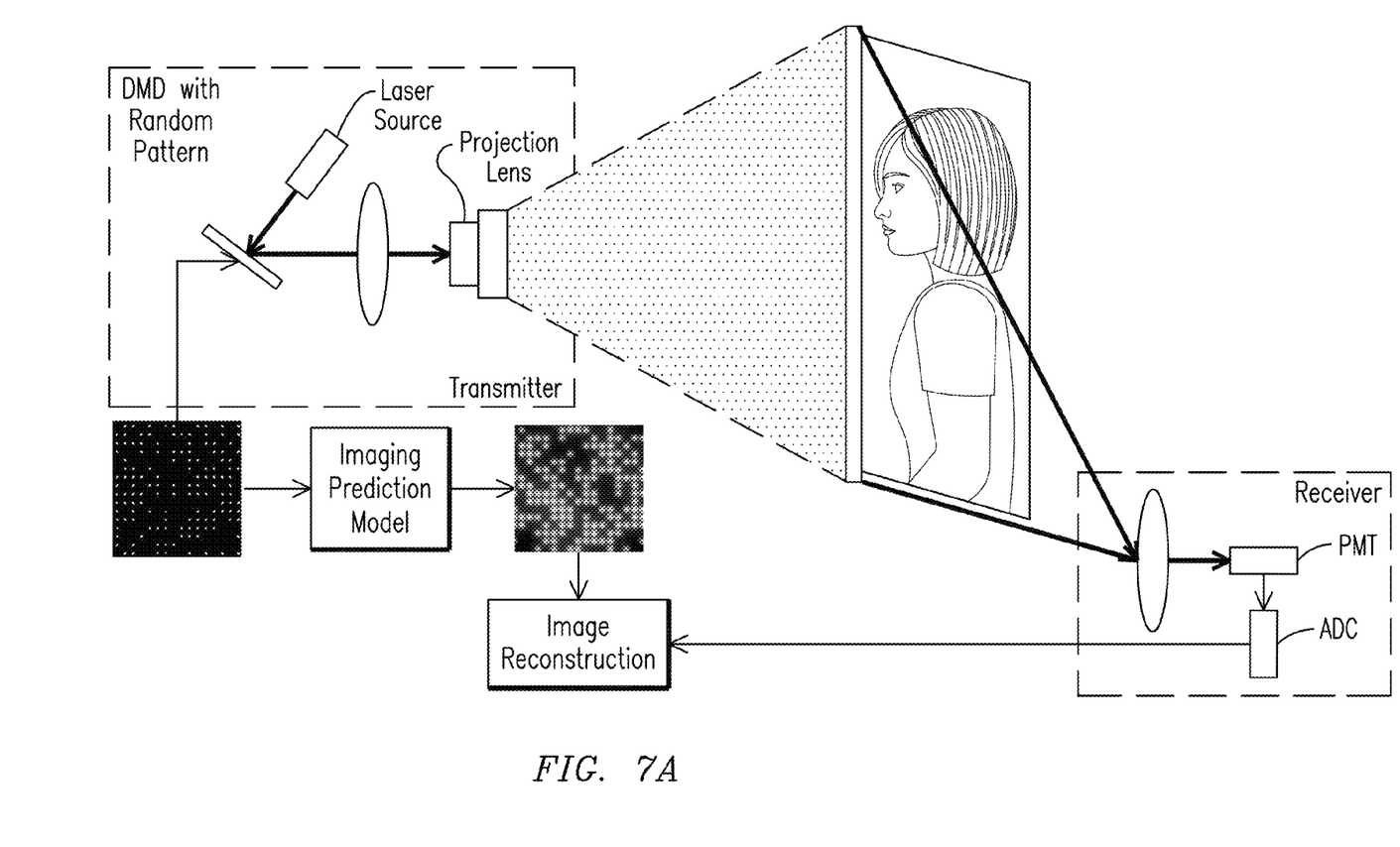
FIG. 7A illustrates a design of a CS based underwater laser imager concept according to the invention.
Figure 7B:
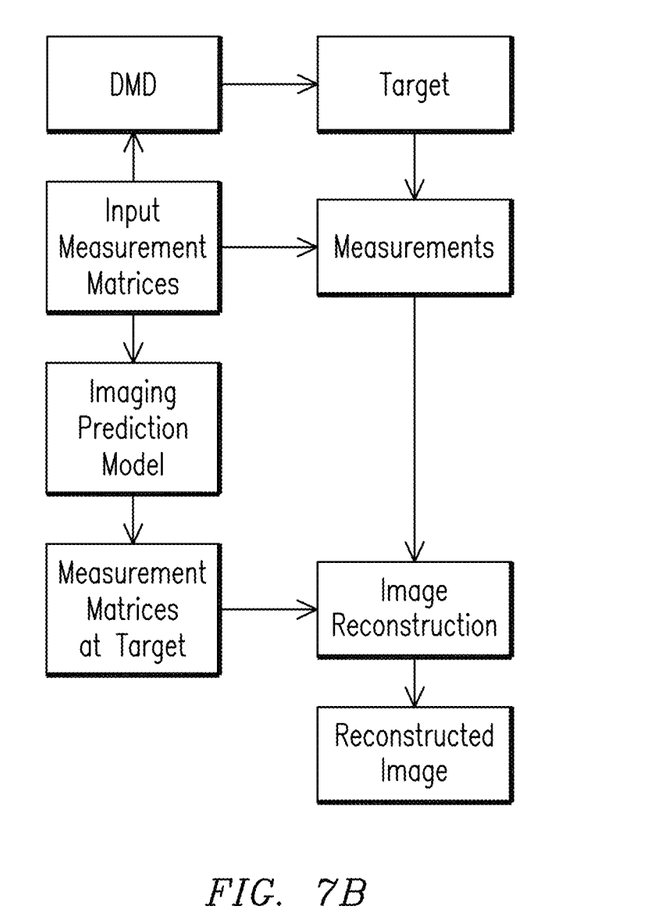
Figure 8:
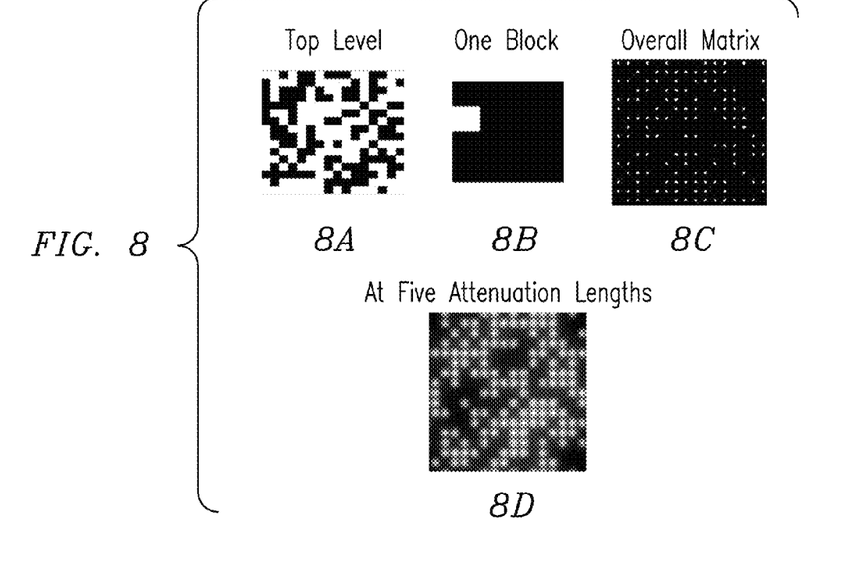
FIGS. 8A-8D illustrate Multi-scale measurement matrix designs.

FIG. 7A illustrates a design of a Compressive Sampling (CS) based underwater laser imager according to the invention. Referring to the flow chart of FIG. 7B, input measurement matrices are loaded sequentially onto a spatial light modulator such as a DMD to modulate a CW or pulsed laser source to illuminate the target. The reflection is then measured using a photon detector such as photomultiplier tube or photodiode and converted to digital data stream using an analog to digital converter. The original measurement matrices are run through an imaging prediction model to predict the measurement matrices at the target. The predicted measurement matrices and the measurement are then used to reconstruct the target image. Designs according to FIG. 7 enable operation of the CS based imager in an underwater environment by incorporating the following four concepts:

1) Multi-Scale Measurement Matrix Design

With reference to FIGS. 8A-8D, the dither pattern is divided into small blocks of pre-defined size. Only one "on" pixel will be present within each block and the location of this pixel within the block $\{b_{ij}\}$ will be generated from a pseudo-random sequence $\{p_{1i,j}\}$. The polarity of each block will be determined by a second pseudo random sequence $\{p_2\}$. The overall dither pattern will be the product of $\{p_2\}$ and $\{p_{1i}\}$:

$$\begin{cases} x(i, j, k) = 1, \text{ iff } p_{1i,j}(k) * p_2(i, j) = 1 \\ x(i, j, k) = 0, \text{ otherwise} \end{cases} \quad (5)$$

where x is the pixel intensity, i, j are the block indices, and k is the pixel location within a block.

2) Model Assisted Image Reconstruction

Figure 9A:
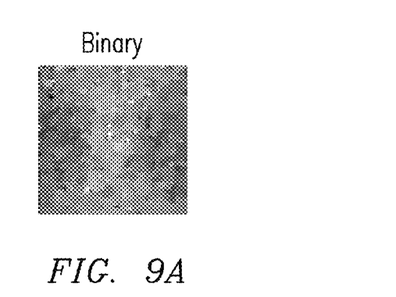
FIGS. 9A and 9B provide a comparison of reconstructed image using binary measurement matrices and model predicted matrices at 7 attenuation lengths.
Figure 9B:
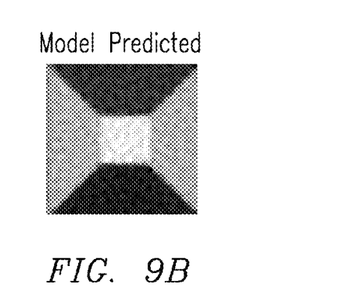

Measurement matrices that actually modulate the target surface S are not the original binary measurement matrices. Instead such patterns result after propagating in the water from the source to the target surface. The measurement matrices used in image reconstruction should be the actual pattern which modulated the target. A radiative transfer model such as EODES [11] can predict the resultant measurement matrices to be used in image reconstruction. FIGS. 9A and 9B illustrate a comparison of a reconstructed image using binary measurement matrices and model predicted matrices at seven attenuation lengths.

3) Polarity Flipping to Reduce Volume Backscatter

With Polarity Flipping each pattern can be loaded twice, first with mirror "on" transmit mode (corresponding to a digital "1"), and then with mirror "off" blocking mode (corresponding to a digital "0"). The difference between the two PMT readings will be the coefficient for a bipolar (1,−1) base v.s. a (0,1) base since the angle of the illumination will be fixed during all of the measurements. In addition, all random measurement bases will consist of about half of "on" position and, therefore, the contribution of the backscattering to the coefficient can be regarded as Gaussian noise with a constant non-zero mean. Therefore, the above polarity flipping can essentially cancel out the impact of the backscattering. This can reduce the impact of the backscattering since a similar number of mirrors will be on during the polarity flipping. Thus the volume backscattering will be the same in the two runs and their difference helps to cancel out or reduce the backscattering levels.

4) Multiplexing to Speed Up Measurements

One disadvantage that might be associated with CS based imaging systems is that measurements would need to be acquired sequentially. This slows down the system response time. The number of sufficient measurements M is proportional to the logarithm of total pixels of the image N: $M \propto \log_2(N)$.

Figure 10:
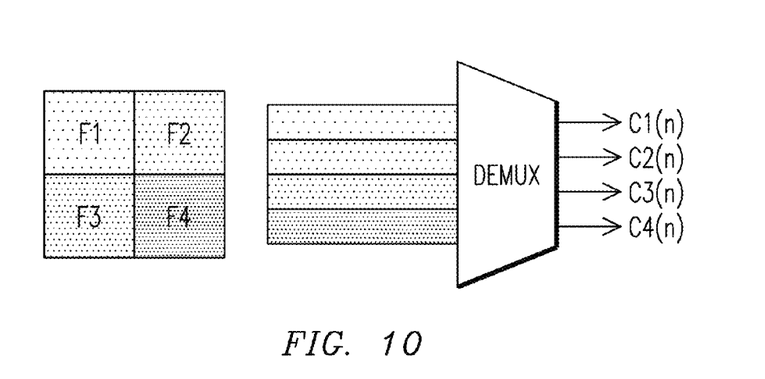
FIG. 10 illustrates spatially multiplexed measurement.

With reference to FIG. 10, another feature of embodiments of the invention is the illumination of different regions with the laser intensity modulated with different frequencies and demodulating the laser signal at the receiver to recover the coefficients corresponding to each sub region. This spatially multiplexed measurement allows for a reduction in the required measurements M, and therefore speeds up the image acquisition time. It provides a novel way to speed up CS measurements which otherwise create a bottleneck in most CS based imaging systems.

Besides providing the ability to compress data during image acquisition, CS has several additional benefits for underwater serial laser imaging systems. A Flexible Imager Configuration is provided having a simple illuminator design and most of the computation load is at the receiver end, which is desirable in a multi-static geometry. The CS-based system works when there is no line-of-sight between the target surface and the photomultiplier tube. The imager configuration is applicable in near mono-static geometries. The resulting systems are reliable, compact and of low cost, using commercially available solid state spatial light modulators and providing compression during acquire which permits lower speed electronics and reduced levels of storage. Such systems have relatively good Photon Efficiency/Concentration, using a "bucket" photon collector—photomultiplier tube, but the efficiency is less than that of a LLS due to photon loss during DMD modulation. Pixel photon concentration depends on compression ratio.

Backscattering is mitigated by polarity flipping, applicable to both CW and pulsed laser. This is unique to CS imagers. Conventional pulsed lasers and range-gated receivers also work for CS imagers. The methodology provides an intrinsically encrypted process because access to the same measurement matrices is necessary in order to recover the image. This is desirable for integrated distributed imaging and communications applications.

It is also possible to provide long range high resolution imaging by integrating the imaging system with long range low bandwidth underwater communication devices, such as acoustic communication devices, without requiring additional compression/decompression hardware.

The foregoing described concepts are also applicable in the context of a passive implementation, where the target to be imaged is illuminated by a pulsed or CW laser. At the receiver a series of binary measurement basis patterns are loaded onto the Spatial Light Modulation device. The photomultiplier tube reading will be the coefficient of each individual basis. These amplitudes can be used in an optimization-based reconstruction, followed by an inverse transformation to recover the spatial image intensity of the target surface S.

Another application of using a digital microdisplay devices such as a DMD, also related to imaging through a turbid medium, is the measurement of the scattering characteristics of a medium. These measurements could include the shape and magnitude of the Volume Scattering Function (VSF), the particle size distribution derived thereby, or other angularly resolved scattering parameters. Accuracy and usefulness of this type of measurement is most often limited by the spatial resolution of the receiver configuration and the sensitivity and dynamic range of the light sensing device.

Figure 11:
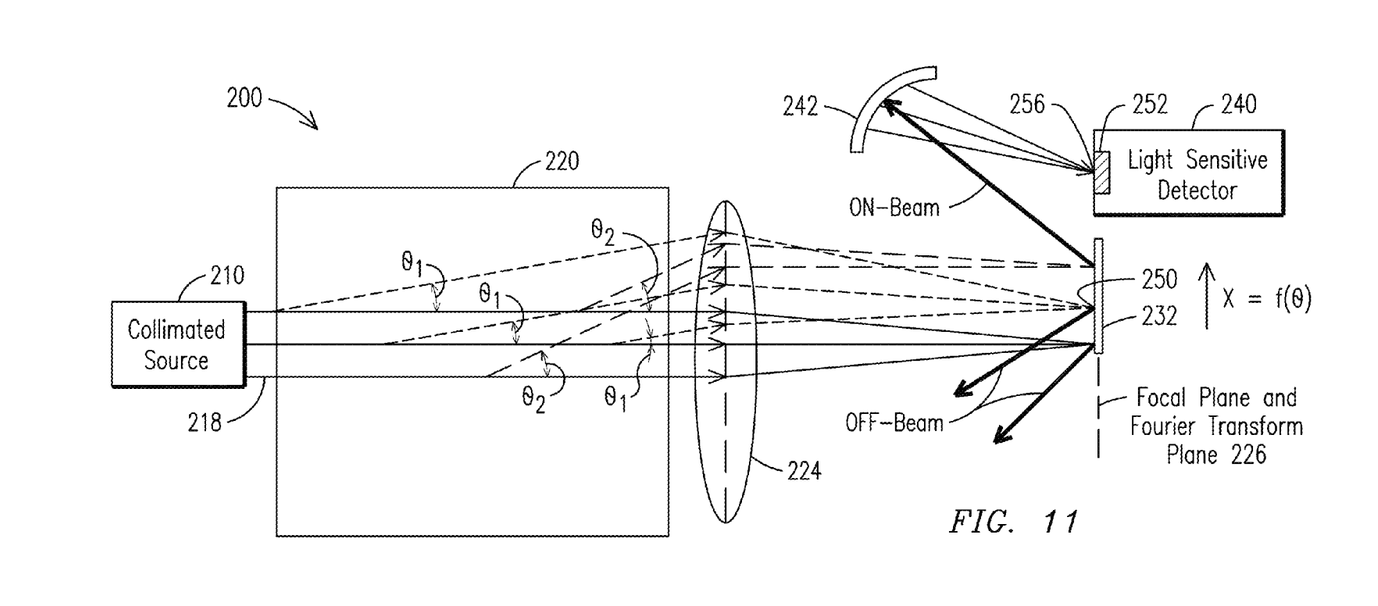
FIG. 11 is a schematic diagram illustrating a scattering sensor system according to an embodiment of the invention.

A method for measurement of the scattering characteristics of a medium employs an optical system such as the exemplary sensor system 200 depicted in FIG. 11. The source 210 transmits collimated incident light 218 which experiences spatial and temporal dispersion while traveling through a scattering medium 220. The spatial distribution of the received light on the light sensitive detector is a function of the VSF of the particle ensemble, absorption characteristics of the suspension, and concentration of the particles. Transmitted and scattered light are both focused through the lens 224. The focal plane 226 (indicated by a hatched line) is also the Fourier transform plane, on which the angular information incident on the lens 224 is transformed to spatial frequency. A DMD 232 is positioned along the focal plane 226 to control the direction of the reflected light field. Some of the light 218 (referred to as ON-beam) is directed to a very sensitive detector 240, such as a photomultiplier tube, via collecting optics 242 (e.g. a hemi-ellipsoidal reflector depicted in FIG. 11). All other light (referred to as OFF-beam) is reflected elsewhere or discarded (e.g. by placing elements in a blocking mode), or collected by a separate light sensitive device e.g., for direct transmission measurements.

Figure 12:
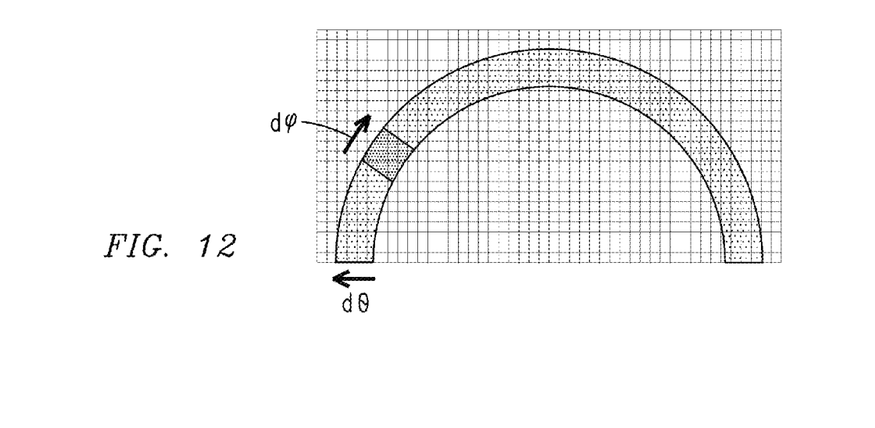
FIG. 12 illustrates an ON-region in an array of mirror elements of a DMD in relation to a scattering angle range.

The light initially scattered by interaction between the incident photons and the particles at a specified angle can be measured by selecting only certain elements within the DMD array to be turned on at a time. On the Fourier plane, this sub-array corresponds to the region where all the light scattered at angle $(\theta,\phi)$ falls. FIG. 12 illustrates an ON-region 260 in an array of mirror elements of a DMD 232 in relation to a scattering angle range to provide an example of how the array of mirror elements can be divided into specific two dimensional sub-arrays, or regions, corresponding to specific scattering angle ranges. Mirror elements in the ON-region are shaded to indicate they are in the transmit mode while unshaded regions correspond to mirror elements in the blocking mode, constituting an OFF-region. The width, referred to as do, with reference to a polar coordinate system, of the ON-region can be adjusted for individual applications. Some particle size measurements would require $d\theta$ to increase logarithmically.

Along the ON-sub-array, light incident on each element is reflected in different directions depending on the azimuth angle $\phi$. To circumvent this dependency, the reflected light is collected by a dual-focal point ellipsoidal reflector, or similar means. The DMD 232 is located on the first focal point 250, while the photocathode 252 of the photomultiplier tube 240 is located on the second focal point 256, where all the light from all azimuth angles $\phi$ is condensed. Therefore, the PMT is responding to the integrated power from all azimuth angles $\phi$. However, if scattering in more refined resolution in the solid angle range is required, the azimuth range can be selected by selecting only a small section of the annular $d\theta$ sub-array. Similarly, embodiments of the invention could consist of a near collocated transmitter and receiver optics, which would provide fine angular scattering in the backward direction.

Significant improvements to the state-of-the-art are the ability of the sensor system 200 to adjust the dynamic range in real-time and in a linear manner, and also, in general, the ability to increase the dynamic range. This could be achieved by modulation (in case of continuous wave applications) or turning off (in pulsed applications) some of the mirror elements in the scattering angle regions, where the scattered intensity is very high compared to other regions, and factoring the decreased irradiance at the light sensitive device, e.g., the photomultiplier tube 240, in the post-processing stage.

In pulsed source applications, the method of using an ultra-fast single-element detector in conjunction with a DMD enables accessing near-simultaneous temporal and spatial information on the scattered light field. This information is especially valuable in highly scattering environments, where multiple scattering is the source for significant, and often limiting, noise impairing the performance of imaging and communication links.

The primary benefit of the innovation is the ability to use a fast, sensitive single-element light sensitive device with a high spatial resolution and minimal processing requirement in scattering measurement applications. The ability of real-time optimization of the spatial resolution makes the system ideal for remote sensing and unmanned operations. The ability of the described system to respond to variations in the dynamic range requirements is highly beneficial, relating to the measurement and observation of medium optical properties in environments, where accessibility or ambient light levels are low or very variable. The near-simultaneous temporal and spatial (angular) measurement gives access to useful information on properties of turbid media, which could be used to optimize performance of remote imaging and communication systems. Summarily features in accord with the invention include: eliminating moving parts needed in prior system designs; reduced cost to maintain high precision optics; reduced system complexity; reduced measurements relative to those required in prior compressive sampling—based image system designs; and higher dynamic range as required for a volume scattering function (VSF) meter.

Embodiments of the invention have been described which simplify the system optics and electronics. For example the imaging systems 10 and 100 do not require moving parts or high precision optical alignment. The computation intensive reconstruction phase can be off-loaded to a central vessel or done off-line. It retains the "bucket collector" PMT type detector that is essential for lumen deficient imaging environments such as turbid waters. A CS based imager and methodology suitable for a low light environment has been described to reduce noise and interference from volume and forward scattering. The invention can also overcome motion artifact problems associated with serial imaging architectures. Further, an active CS illumination system does not require direct line-of-sight observation for the receivers, and can be advantageously used in a bi-static imaging environment. In one series of embodiments frequency multiplexing of the modulated laser reduces the time required for CS measurement.

While exemplary embodiments of the invention have been described, the invention is not so limited. Numerous modifications, changes, variations, substitutions and equivalents will be apparent to those skilled in the art without departing from the spirit and scope of the present invention as described in the claims. It is also noted that, to more clearly present features pertinent to the invention, numerous components have been expressly illustrated while other components may not have been illustrated. Further, in order to illustrate features of the invention, components and features illustrated in the figures may not be to scale. Accordingly, the invention is only limited by the claims which follow.

The claimed invention is:

1. An imaging or sensor system comprising
   a transmitter assembly for defining an outgoing optical beam transmission path with respect to a target surface and a receiver assembly for defining a return optical signal transmission path from the target surface, wherein each of the two optical transmission paths includes transmission through or reflection from at least one microdisplay device comprising a plurality of controllable elements for selective placement in a mode for transmission of light along the transmission paths;
   a control unit for selectively placing microdisplay device elements in the transmission mode;
   a first digital micromirror device in the outgoing optical beam transmission path; and
   a second digital micromirror device in the return optical signal transmission path, wherein the control unit sequentially selects segments of elements in each of the first and the second digital micromirror device to effect scanning along a field of view to generate image information from the target surface.

2. The system of claim 1 wherein the control unit is programmed to determine selection of the controllable elements to define an instantaneous field of view based on an assessment of light scattering between the system and the target surface.

3. The system of claim 1 wherein the field of view is selected by the control unit to provide a time varying instantaneous field of view.

4. A method for measurement of the scattering characteristics of a medium, comprising:
- transmitting collimated light through a scattering medium so that the light experiences spatial or temporal dispersion while traveling through the medium;
- receiving the light on a light sensitive detector;
- after the light travels through the medium, focusing both direct and scattered components of the light on a plane which provides a Fourier transform plane on which angular information incident on the lens is transformed to spatial frequency;
- positioning a microdisplay device along the focal plane to selectively reflect light incident thereon and controlling the direction of reflection of the incident light; and
- directing a portion of the reflected light to a light sensitive detector for measurement while not directing other portions of the reflected light for receipt by the detector.

5. The method of claim 4 wherein the portion of the reflected light directed to the light sensitive detector is reflected thereto by a hemi-ellipsoidal reflector.

6. The method of claim 4 wherein the light which experiences spatial or temporal dispersion while traveling through the medium is measured by selecting only certain elements within the microdisplay device array to be in a transmit mode while other elements are in a blocking mode.

7. The method of claim 6 wherein the portion of light directed to the detector is determined by a segment of adjacent elements of the microdisplay device which are simultaneously placed in the transmit mode.

8. A method of imaging with a light beam, comprising:
- providing a beam of light from a source;
- reflecting the light from a first microdisplay device comprising a plurality of moveable reflective elements so the light travels along a first path to a surface;
- receiving a portion of the light, travelling along a second path from the surface, on to a second microdisplay device; and
- using the second microdisplay device to reflect the portion of the light to a detector.

9. The method of claim 8, wherein movement of individual reflective elements of the first microdisplay device is controlled to select one or more of the elements to reflect only a portion of the light from the first microdisplay device at a given time and create a scan of the light along the surface while other ones of the elements are in a blocking mode with respect to the first path.

10. The method of claim 9 wherein, based on the selection of elements in the first microdisplay device to reflect the light: (i) the beam is varied in size; and (ii) the direction of the first path is varied.

11. The method of claim 9 wherein elements of the first microdisplay device are sequentially placed in a reflective mode to create the scan.

12. The method of claim 9 wherein:
- segments comprising multiple adjoining mirror elements in the first microdisplay device are selected so that elements in individual segments are simultaneously selected to reflect light at a given time; and
- different segments are sequentially selected to reflect the light in order to create the scan of the light along the surface.

13. The method of claim 9 wherein elements in the second microdisplay are sequentially selected based on computed instantaneous fields of view.

14. The method of claim 13 wherein:
- the sequential selection of elements in the second microdisplay includes a selection sequence in which multiple adjoining elements are simultaneously selected based in part on the computed instantaneous field of view; and
- the instantaneous field of view is provided based on a determination of size of the light beam reflected by the first microdisplay device and based on an angle of the light beam which varies according to the location of selected elements on the first microdisplay device.

15. The method of claim 14 wherein the number of adjoining elements which are simultaneously selected is based on expanding or limiting the instantaneous fields of view relative to the computed instantaneous fields of view.

16. The method of claim 13 wherein scattered light is eliminated from the second path by reducing the field of view of the second microdisplay device relative to the computed instantaneous field of view.

17. The method of claim 13 wherein transmission of the light along the first or second path includes transmission through a prism and transmission of the light along the other of the first and second paths includes reflection from an internal surface of the prism.

18. The method of claim 8 applied in a system having a receiver assembly which includes the second microdisplay device wherein the receiver assembly operates as a moving iris which allows non-scattered photons to reach a detector device while blocking scattered light from reaching the detector device.

19. The method of claim 9 wherein, during a scan, when elements in a group in the first microdisplay device are placed in a transmit mode, only a segment of elements in the second microdisplay device, which correspond to no more than the computed instantaneous field of view resulting from the group of elements, is placed in the transmit mode.

* * * * *